United States Patent
Sutera, III

(10) Patent No.: US 10,010,391 B2
(45) Date of Patent: Jul. 3, 2018

(54) DEVICE FOR EVALUATING DENTAL CROWN CONTACTS

(71) Applicant: Charles Sutera, III, Somerville, MA (US)

(72) Inventor: Charles Sutera, III, Somerville, MA (US)

(73) Assignee: Charles Sutera, III, Medford, MA (US)

( * ) Notice: Subject to any disclaimer, the term of this patent is extended or adjusted under 35 U.S.C. 154(b) by 141 days.

(21) Appl. No.: 15/257,786

(22) Filed: Sep. 6, 2016

(65) Prior Publication Data

US 2018/0064518 A1    Mar. 8, 2018

(51) Int. Cl.
*A61C 19/05*    (2006.01)
*A61C 1/08*    (2006.01)

(52) U.S. Cl.
CPC .......... *A61C 19/052* (2013.01); *A61C 1/084* (2013.01)

(58) Field of Classification Search
CPC ....... A61C 19/05; A61C 19/052; A61C 1/084; A61C 5/30; A61C 8/0089
See application file for complete search history.

(56) References Cited

U.S. PATENT DOCUMENTS

| | | | | |
|---|---|---|---|---|
| 1,518,021 A | * | 12/1924 | Truxillo | A61C 3/06 132/323 |
| 6,095,815 A | * | 8/2000 | Mueller | A61C 19/04 433/159 |
| 6,981,870 B2 | * | 1/2006 | Heasley | A61C 19/004 433/139 |
| 7,083,412 B1 | * | 8/2006 | Karapetyan | A61C 5/85 433/148 |
| 2011/0151406 A1 | * | 6/2011 | Solano | A61C 19/05 433/162 |
| 2017/0071700 A1 | * | 3/2017 | Pieroni | A61C 5/125 |
| 2017/0340422 A1 | * | 11/2017 | Al Taweel | A61C 13/0003 |

* cited by examiner

*Primary Examiner* — Daniel James Colilla

(57) ABSTRACT

A dental device was designed to improve the process for a dentist to evaluate crown interproximal contacts during a dental crown delivery procedure. The device may temporally attach to an adjacent tooth to the crown being inserted. The device positions a marking material approximately at the interproximal contact area which allows for marking of contact pressure and location upon insertion of a new dental crown for evaluation prior to cementation. The device provides an improved method compared to existing methods for evaluating crown contacts.

14 Claims, 2 Drawing Sheets

DEVICE FOR EVALUATING DENTAL CROWN CONTACTS

CROSS REFERENCE TO RELATED APPLICATIONS

The application claims the benefits of provisional patent application No. 62/251,346 filed Nov. 5, 2015 by the present inventor.

FIELD OF THE INVENTION

The present invention relates generally to dental instruments and materials and methods for using them in fixed prosthodontic procedures, and more specifically to devices and materials for facilitating the installation and fitting of artificial tooth crowns and inlays in a patient's mouth.

BACKGROUND OF THE INVENTION

A strong need exists for dentists to have an alternative to traditional methods for evaluating dental crown contacts during a crown insertion procedure. Incorrect contact of a crown and adjacent tooth is one of the most common causes of improper seating of a crown by a dentist. During a crown insert procedure the dentist typically evaluates the fit of the interproximal contacts to ensure the crown is not wedged between one or more adjacent teeth preventing full seat of the crown. At present there are several common ways of evaluating the contacts. A dentist may manually position articulating paper at the contact area to mark the crown, a dentist may floss the interproximal contact, or a dentist may spray a colored spray on the crown and then evaluate where the spray has been displaced after seating the crown. Each of the listed methods have disadvantages.

The articulating paper method is ergonomically difficult. The dentist must position the articulating paper at the contact site of a dental crown either by hand or with an articulating paper holder while simultaneously seating the crown with another hand, and also maintaining sufficient isolation of the tongue and cheek. The process typically involves four-handed dentistry, and is challenging for the dental professionals as well as patients due to limited space for multiple hands all attempting access to the same area of the mouth. U.S. Pat. No. 1,458,062 describes a "paper adapted for use by dentists in the securing of articulation impressions of the teeth of a person for the accurate manufacture of false teeth or sets of such teeth." The patent describes common articulating paper which is used by many dentists to evaluate occlusion as well as crown contacts but does not, however, offer a convenient method for utilizing or positioning the articulating paper. U.S. Pat. No. 5,851,114 describes a kit containing instruments for facilitating insertion of dental crowns. The said kit contains a "ribbon forceps used to grip a thin precut test ribbon and hold the ribbon in the patient's mouth vertically on either the front or back side of an artificial crown being placed." The ribbon forceps "tests and marks the area of interproximal contact of the crown or inlay as well as the amount of pressure of the contact." Although the tool aids to help position the articulating paper, the method of use requires a healthcare provider to manually position the ribbon forceps which can be ergonomically challenging, and does not appear to reduce the number of hands required to evaluate the contact via this method.

A second method, the floss method of checking crown contact, is imprecise for identifying where the new crown needs adjustment. The process involves a dentist seating the crown onto the crown prep. The dentist then flosses the mesial and distal areas to determine if the fit is tight or loose. The method allows the identification of a fit problem, but does not allow a dentist to evaluate precisely which area of the interproximal requires adjustment. The adjustment of a crown contact by a dentist after only flossing becomes a blind guess in attempting to correct the fit problem which could lead to excessive adjustment in areas of the interproximal.

A third method, the spray method of checking crown contact, is disadvantageous because the process is messy. U.S. Pat. No. 3,707,771 describes an "aerosol spray of composition of matter" which is commonly used by dentists to evaluate occlusal contacts and interproximal contacts during crown insert procedures. During this method, a dentist sprays a marking spray onto the new crown on the interproximal, and seats the crown. The dentist then removes the crown, evaluates where the spray has been displaced, and may adjust the crown in the areas indicated. After adjusting the crown, however, there is often residual marking spray remaining on the crown and the adjacent teeth which can be difficult and time consuming to fully remove prior to cementation. The spray technique furthermore is difficult ergonomically as the dentist must be cautious to not hold the crown in the area of the interproximal to avoid unintentional smearing of the spray.

The presented invention comprises a precise, ergonomic, economical, and efficient method for evaluating crown contact.

SUMMARY OF THE INVENTION

In accordance with one embodiment, the marking of dental crown interproximal contact pressure during a crown insert procedure comprises a device which may attach to a tooth adjacent to a crown preparation, and said device orients a piece of marking paper approximately at the interproximal contact area. The said device allows for marking and evaluation of excessive contact pressure on the new crown upon insertion of said crown for evaluation. The dental professional may then choose to adjust the crown as said dental professional feels appropriate.

Accordingly several advantages of one or more aspects are as follows: to provide a device that enables a dentist to evaluate the interproximal fit of a new dental crown prior to insertion via a device which is relatively easy to place on adjacent teeth, is relatively inexpensive, relatively easily positions a marking material in the contact area, and is relatively precise in marking a dental crown upon insertion to indicate location of interproximal contact pressure. Other advantages of one or more aspects will be apparent from a consideration of drawings and ensuing description.

DESCRIPTION OF EMBODIMENTS

Figure 1:
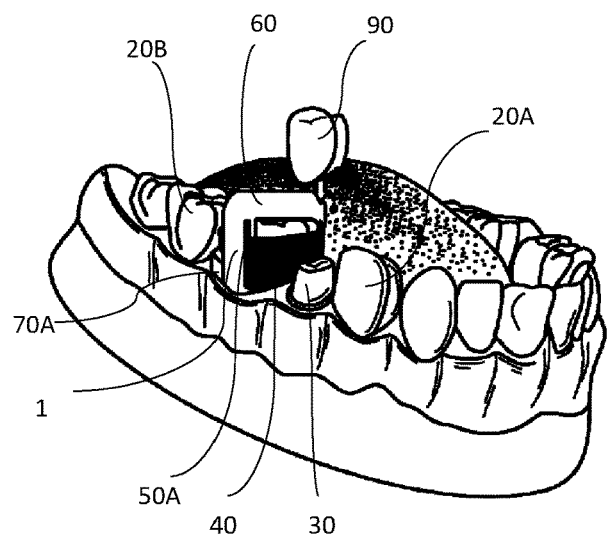
FIG. 1 is a perspective view of a device demonstrating an embodiment.
Figure 2:
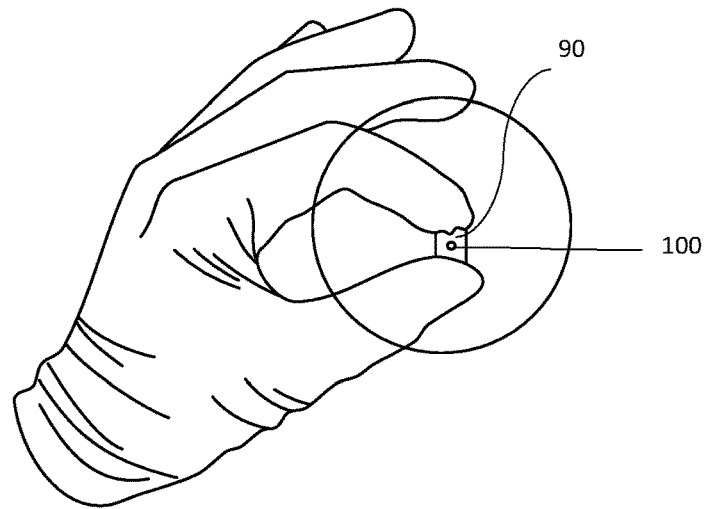
FIG. 2 is a perspective view of a dental professional holding a dental crown that illustrates the interproximal contact marking transferred to the crown.
Figure 3:
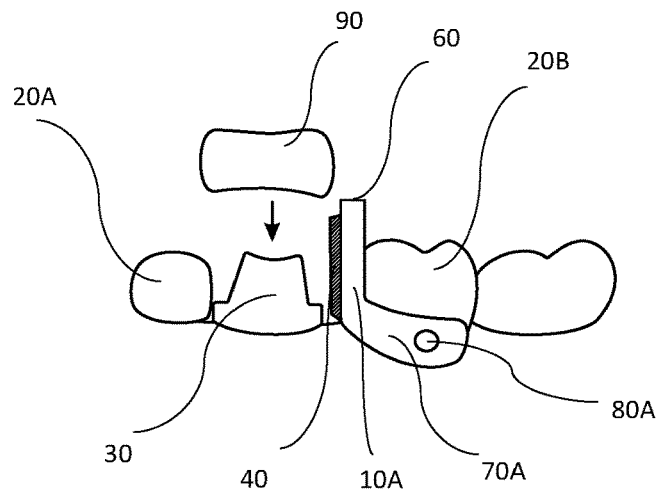
FIG. 3 is a side view of a device demonstrating an embodiment.
Figure 4:
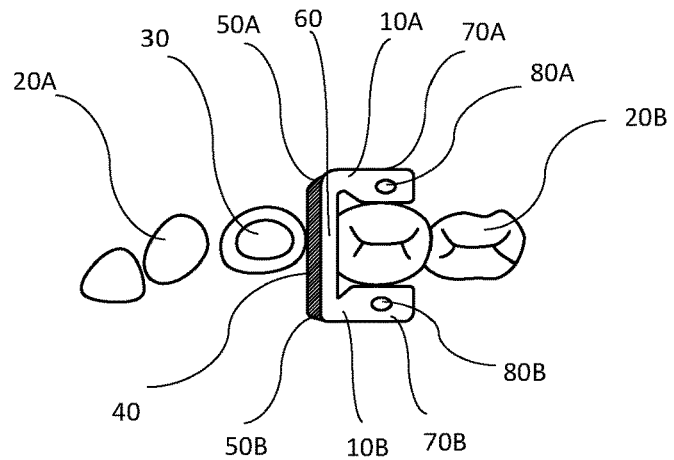
FIG. 4 is an aerial view of a device demonstrating an embodiment.

One embodiment of the device is illustrated in FIG. 1 (oblique view), FIG. 3 (side view), and FIG. 4 (aerial view). The device comprises a plurality of non-rigid or rigid attachment members [10A, 10B] which allow said device to temporarily attach to an adjacent tooth [20A, 20B] to a dental crown preparation [30]. In one embodiment the attachment members [10A, 10B] are made of a non-rigid material such as silicone which will allow the attachment members to spread apart during placement and recoil upon positioning around an adjacent tooth [20A, 20B] to securely attach to said adjacent tooth. The attachment members, however, may consist of any material which will allow for placement upon a tooth without fracturing such as silicone, thermoplastic polyurethane, polypropylene, rubber, various plasticized materials, etc. The device comprises the ability to secure a marking material [40] and a plurality of marking material attachment areas [50A, 50B] such as but not limited to slots, clips, grooves, flat areas suitable for adherence of marking material [40], etc. The thickness of suitable marking material [40] may comprise a range from 1 micron to 1000 microns. The attachment members may connect to one another a variety of ways so long as they position in a way that allows the device to properly attach to a tooth and so long as they allow for attachment of a marking material which positions approximately in the interproximal contact area. In one embodiment the attachment members are connected via a non-rigid or rigid bridge member [60] which arches transversely above and perpendicular to the attachment members [10A, 10B] and positions said attachment members [10A, 10B] on either side of a tooth adjacent to a crown prep [20A, 20B].

The attachment members [10A, 10B] may also comprise a jaw-like end [70A, 70B] which is of a shape that sufficiently allows contour to a tooth when the device is positioned for placement onto a tooth [20A, 20B]. The jaw-like end [70A, 70B] can comprise a longitudinal through-hole [80A, 80B] which creates an area suitable to allow attachment of common rubber dam clamp forceps to aid placement of the device onto a tooth in a similar manner to a rubber dam clamp should the dental professional choose to use this method of placement. Although a longitudinal through-hole is presented in one embodiment, the area may also be a ridge, groove, indentation, etc which can also allow sufficient retention for the device to attach to rubber dam clamp forceps or similar proprietary or non-proprietary forceps.

The manner in which a dental professional uses the device is during a dental crown insertion procedure. The dental professional positions the device on an adjacent tooth [20A, 20B] to a dental crown preparation [30]. The device then serves to position a marking material [40] approximately in the contact area between the adjacent tooth [20A, 20B] and the new dental crown [90]. The dental professional may then seat the new dental crown [90] onto the dental crown preparation [30], and as the dental crown seats into position a marking may be transferred to the dental crown via the marking material [40]. The dental professional may then remove the new dental crown [90] and evaluate the marking on the crown [100] which indicates the location of interproximal contact pressure. The dental professional may then adjust the crown [90] in the area of the marking [100] as they deem appropriate. The procedure may be repeated for the mesial and distal interproximal contacts until the dental professional deems the interproximal contact appropriately adjusted.

The presented embodiments of the device enable an improved method compared to existing methods for evaluating crown contacts. The device enables a method which is more ergonomic for the healthcare providers as well as the patient. The method is furthermore of a high level of precision in determining the interproximal contact pressure both in amount and location. The method requires minimal cleanup and generally reduces amount of time needed to successfully evaluate and adjust the interproximal contact of a new dental crown prior to insertion. Accordingly, the reader will see the various embodiments provide dental professionals an easy, fast, and accurate way of evaluating interproximal contact pressure prior to cementation of a dental crown [90].

Although the description above contains much specificity, these specifications should not be construed as limiting the scope of the embodiments, but as merely providing illustration of some of the several embodiments. For example, the attachment members may be of a variety of different shapes, sizes, and number which could accommodate attachment to human teeth, moreover the device could be manufactured to accommodate different types, shapes, and sizes of teeth such as a large molar compared to a small premolar.

Thus, the scope of the embodiments should be determined by the appended claims and their legal equivalents, rather than by only the examples given.

The invention claimed is:

1. A dental device for evaluating dental crown interproximal contact comprising:
   a) an attachment member or a plurality of attachment members the approximate height of a human tooth
   b) a means of connecting and/or positioning said attachment members in a way that allows attachment to a tooth
   c) a means of positioning a marking material approximately at a contact area between a tooth prepared for a crown and an adjacent tooth whereby a dental professional may evaluate contact pressure of a dental crown prior to cementation via markings transferred to said dental crown by said marking material.

2. The dental device of claim 1 wherein said attachment members have a jaw-like end that approximates the surface of a tooth.

3. The dental device of claim 2 wherein said attachment members jaw-like end has a plurality of suitable areas to allow attachment of common rubber dam clamp forceps to enable placement of said device onto a tooth.

4. The dental device of claim 1 wherein said dental device is made of silicone.

5. The dental device of claim 1 wherein said dental device is made of thermoplastic polyurethane.

6. The dental device of claim 1 wherein said dental device comprises a marking material of sufficient size to approximate the buccal to lingual width of a human tooth.

7. The dental device of claim 6 wherein said marking material is made of dental articulating paper.

8. The dental device of claim 6 wherein said marking material is between 1 and 1000 microns in thickness.

9. The dental device of claim 1 wherein said dental device comprises a marking material attachment area or a plurality of marking material attachment areas.

10. The dental device of claim 9 wherein said means of positioning said marking material are slots located on said marking material attachment areas.

11. The dental device of claim 1 wherein said dental device means of connecting attachment members is via a bridge member.

12. The dental device of claim 11 wherein said bridge member is non-rigid.

13. The dental device of claim 11 wherein said bridge member comprises said means of positioning a marking material.

14. The dental device of claim 1 wherein said attachment members are non-rigid.

\* \* \* \* \*